US010426421B2

(12) United States Patent
Wollenweber et al.

(10) Patent No.: US 10,426,421 B2
(45) Date of Patent: Oct. 1, 2019

(54) METHODS AND SYSTEMS FOR PROCESSING MOLECULAR IMAGING DATA BASED ON ANALYSIS OF A RESPIRATORY MOTION WAVEFORM

(71) Applicant: General Electric Company, Schenectady, NY (US)

(72) Inventors: Scott David Wollenweber, Waukesha, WI (US); Nathan Tibbitts Roberts, Madison, WI (US)

(73) Assignee: General Electric Company, Schenectady, NY (US)

( * ) Notice: Subject to any disclaimer, the term of this patent is extended or adjusted under 35 U.S.C. 154(b) by 686 days.

(21) Appl. No.: 14/996,476

(22) Filed: Jan. 15, 2016

(65) Prior Publication Data
US 2017/0202533 A1    Jul. 20, 2017

(51) Int. Cl.
| | | |
|---|---|---|
| *A61B 5/00* | (2006.01) | |
| *A61B 6/00* | (2006.01) | |
| *A61B 6/03* | (2006.01) | |
| *A61B 5/08* | (2006.01) | |

(52) U.S. Cl.
CPC .......... *A61B 6/5264* (2013.01); *A61B 5/7289* (2013.01); *A61B 6/037* (2013.01); *A61B 6/465* (2013.01); *A61B 6/5288* (2013.01); *A61B 5/0816* (2013.01)

(58) Field of Classification Search
CPC ..... A61B 6/5264; A61B 6/5288; A61B 6/465; A61B 6/037; A61B 5/7289; A61B 5/0816
See application file for complete search history.

(56) References Cited

U.S. PATENT DOCUMENTS

| | | | | |
|---|---|---|---|---|
| 2010/0249630 A1* | 9/2010 | Droitcour | ................ | A61B 5/05 600/529 |
| 2010/0260402 A1* | 10/2010 | Axelsson | .............. | G06T 11/008 382/131 |
| 2011/0116695 A1* | 5/2011 | Wollenweber | ......... | A61B 6/469 382/131 |
| 2015/0351699 A1* | 12/2015 | Addison | .............. | A61B 5/7221 600/301 |

OTHER PUBLICATIONS

Jani, S. et al., "A Comparison of Amplitude-Based and Phase-Based Positron Emission Tomography Gating Algorithms for Segmentation of Internal Target Volumes of Tumors Subject to Respiratory Motion," International Journal of Radiation Oncology*Biology*Physics, vol. 87, No. 3, Nov. 1, 2013, 15 pages.

Pepin, A. et al., "Management of Respiratory Motion in PET/Computed Tomography: the State of the Art," Nuclear Medicine Communications, vol. 35, No. 2, Feb. 2014, 10 pages.

* cited by examiner

*Primary Examiner* — Joel Lamprecht
(74) *Attorney, Agent, or Firm* — McCoy Russell LLP

(57) ABSTRACT

Methods and systems are provided for analyzing a respiratory motion waveform acquired during acquiring imaging data with a molecular imaging device. In one embodiment, a method comprises acquiring imaging data with a molecular imaging apparatus, analyzing a respiratory motion waveform acquired during the acquiring imaging data, and applying gating to the acquired imaging data based on the analyzed respiratory motion waveform. In this way, gating may be applied to the acquired imaging data in order to generate an image for medical diagnosis with increased image quality and accuracy.

19 Claims, 8 Drawing Sheets

METHODS AND SYSTEMS FOR PROCESSING MOLECULAR IMAGING DATA BASED ON ANALYSIS OF A RESPIRATORY MOTION WAVEFORM

FIELD

Embodiments of the subject matter disclosed herein relate to molecular imaging, and more particularly, to analyzing a respiratory motion waveform acquired during acquiring molecular imaging data.

BACKGROUND

Various medical imaging techniques exist to aid clinicians in the diagnosis of pathological conditions caused, for example, by anatomic or functional manifestations of a disease. Many such techniques produce a sequence of image frames that can be used to highlight to the clinician various temporal variations in anatomical and/or functional properties of a patient. As one example, PET imaging can be used to obtain a sequence of image frames showing, for example, how the physiological functional properties of a patient's organ, such as, for example, the brain, vary over time. However, during a PET image acquisition period, data may be acquired for multiple scan positions of several minutes per position and then written to a file. During this time, a patient may breathe regularly. However, respiratory motion of the patient during the scan (which occurs for several breath cycles) may result in degradation of the final image (e.g., image blur and quantitation inaccuracy) and thus less accurate medical diagnosis based on the final images.

In one example, to mitigate respiratory motion effects, the acquired data may be respiratory gated (e.g., broken into like-displacement bins per respiratory cycle) or only a portion of the data acquired under a more quiescent-like (e.g., flat) portion of the respiratory cycle may be kept. However, gating may only be beneficial for data acquired from patients with certain breathing patterns (e.g., patterns that are more consistent or have a more defined quiescent period in each cycle). Discarding portions of the acquired image data increases noise in the image data which may further degrade the resulting image.

BRIEF DESCRIPTION

In one embodiment, a method comprises acquiring imaging data with a molecular imaging apparatus, analyzing a respiratory motion waveform acquired during the acquiring imaging data, and applying gating to the acquired imaging data based on the analyzed respiratory motion waveform. By analyzing the respiratory motion waveform, it may be determined if it would be beneficial (e.g., result in a higher quality image for medical diagnosis) to apply gating to the acquired imaging data. In this way, images generated from the acquired imaging data may have increased quality due to decreased motion-induced image blur.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
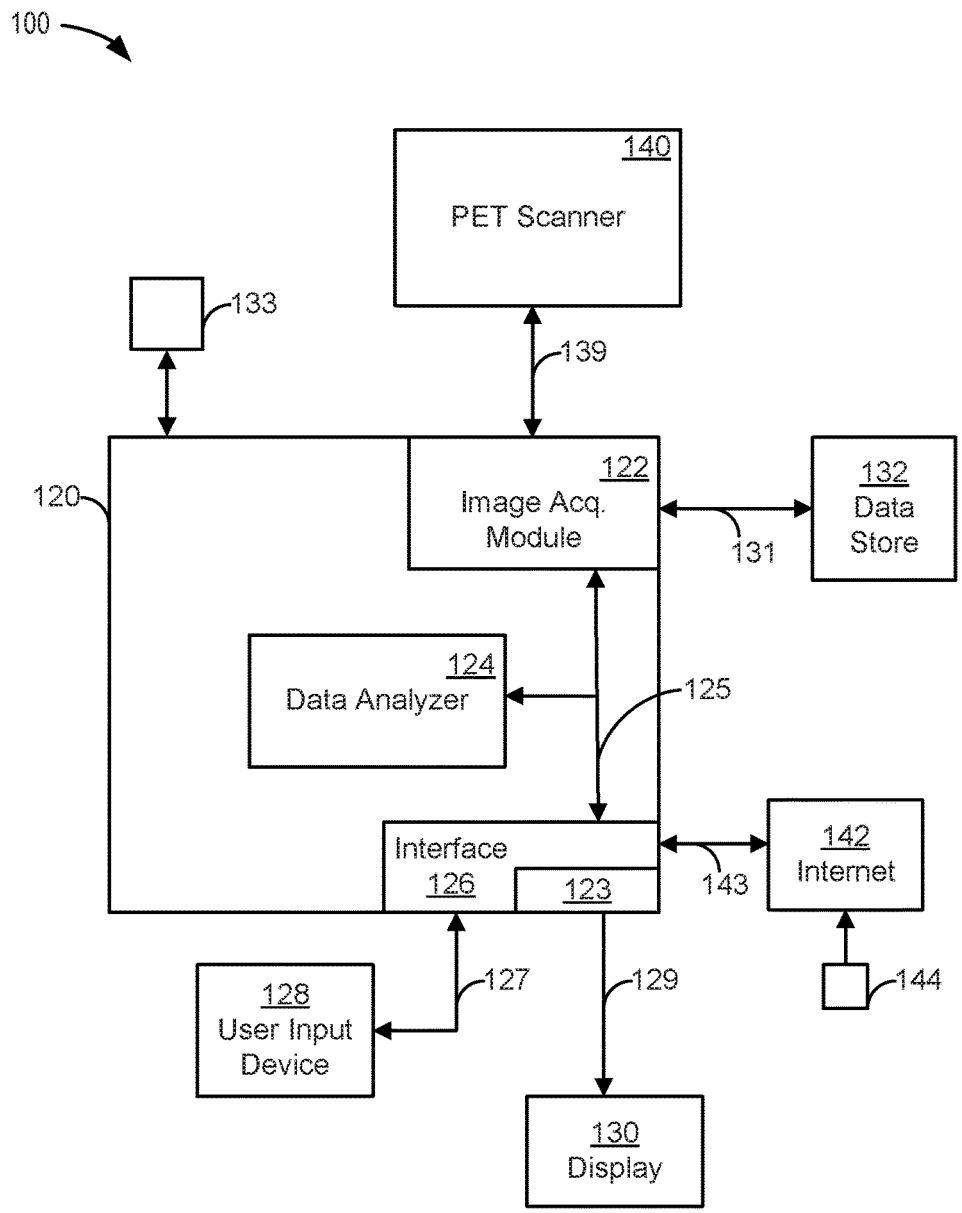
FIG. 1 shows a system for analyzing acquired molecular imaging data and clinical diagnosis of a patient according to an embodiment of the invention.
Figure 2:
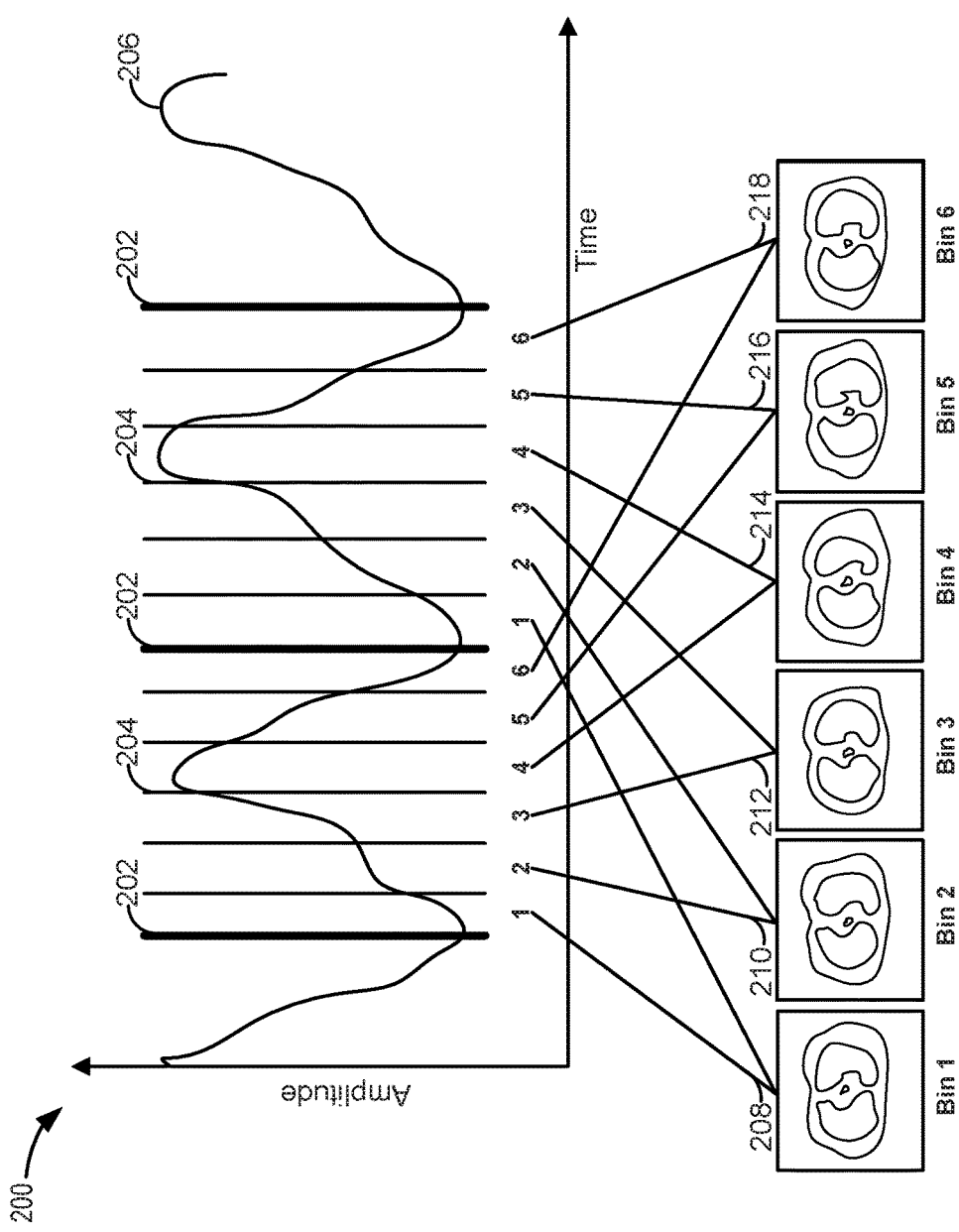
FIG. 2 shows an example of a typical gating technique applied to acquired molecular imaging data according to an embodiment of the invention.
Figure 3:
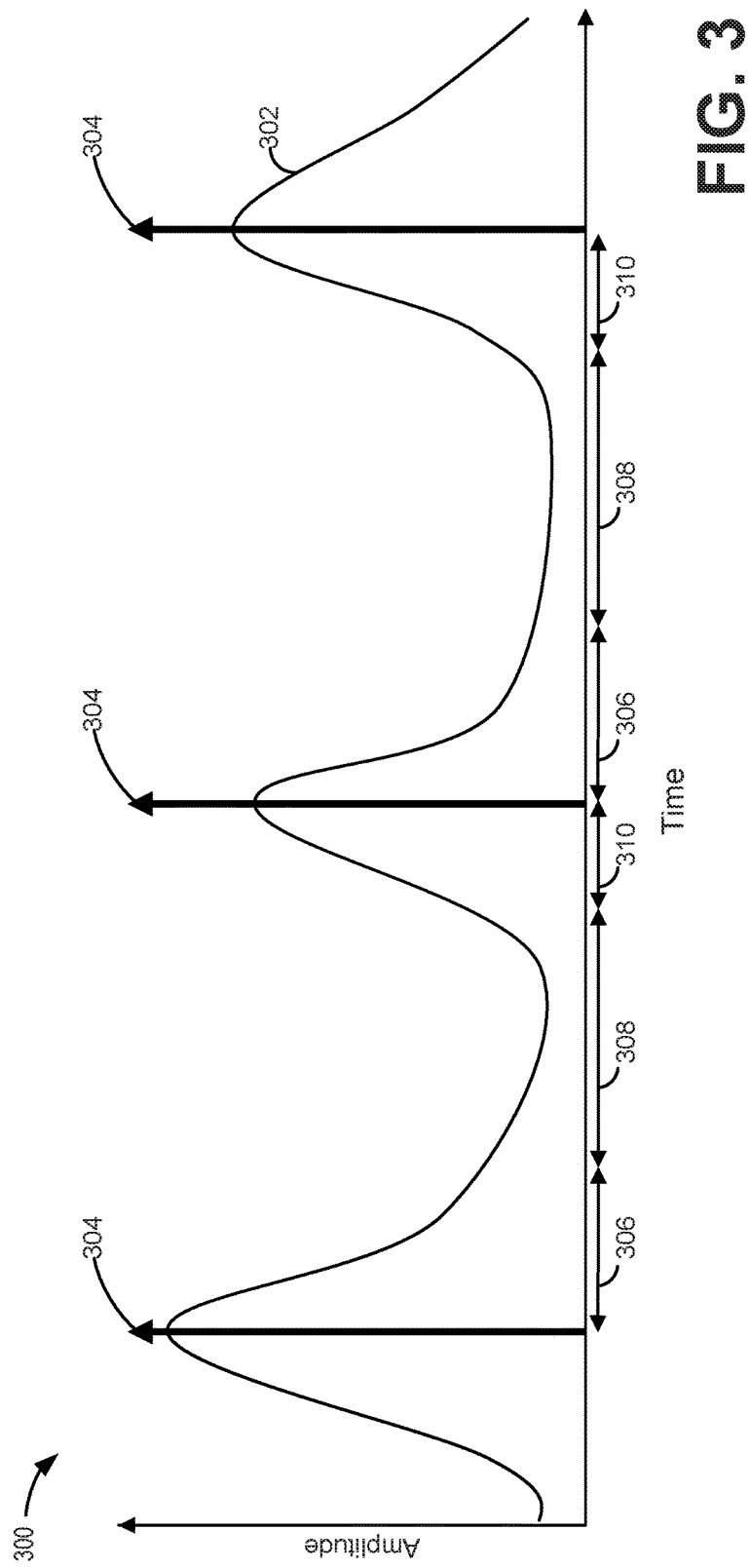
FIG. 3 shows an example of a quiescent period gating technique applied to acquired molecular imaging data according to an embodiment of the invention.
Figure 4:
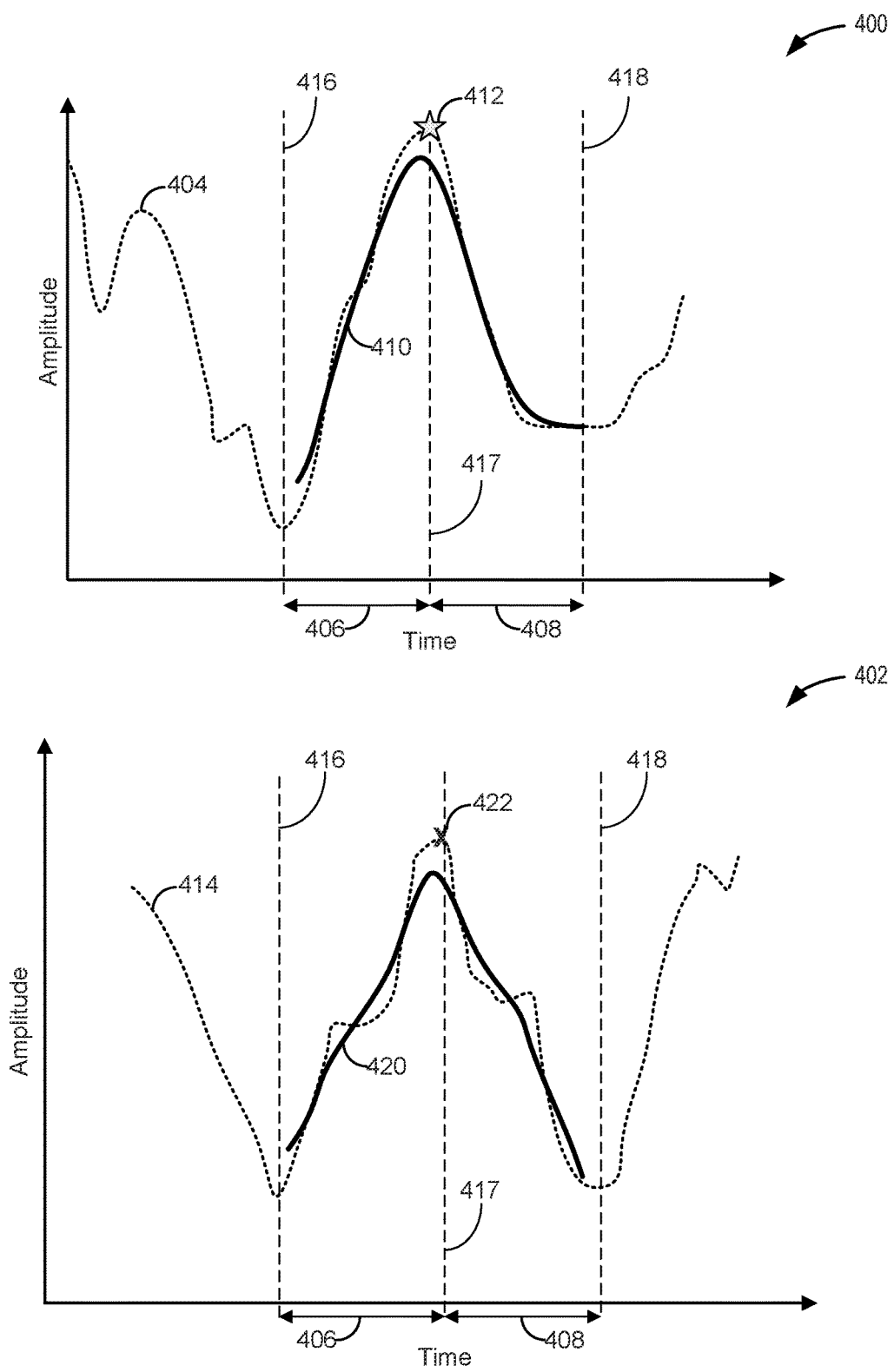
FIG. 4 shows example respiratory motion waveforms according to an embodiment of the invention.
Figure 5:
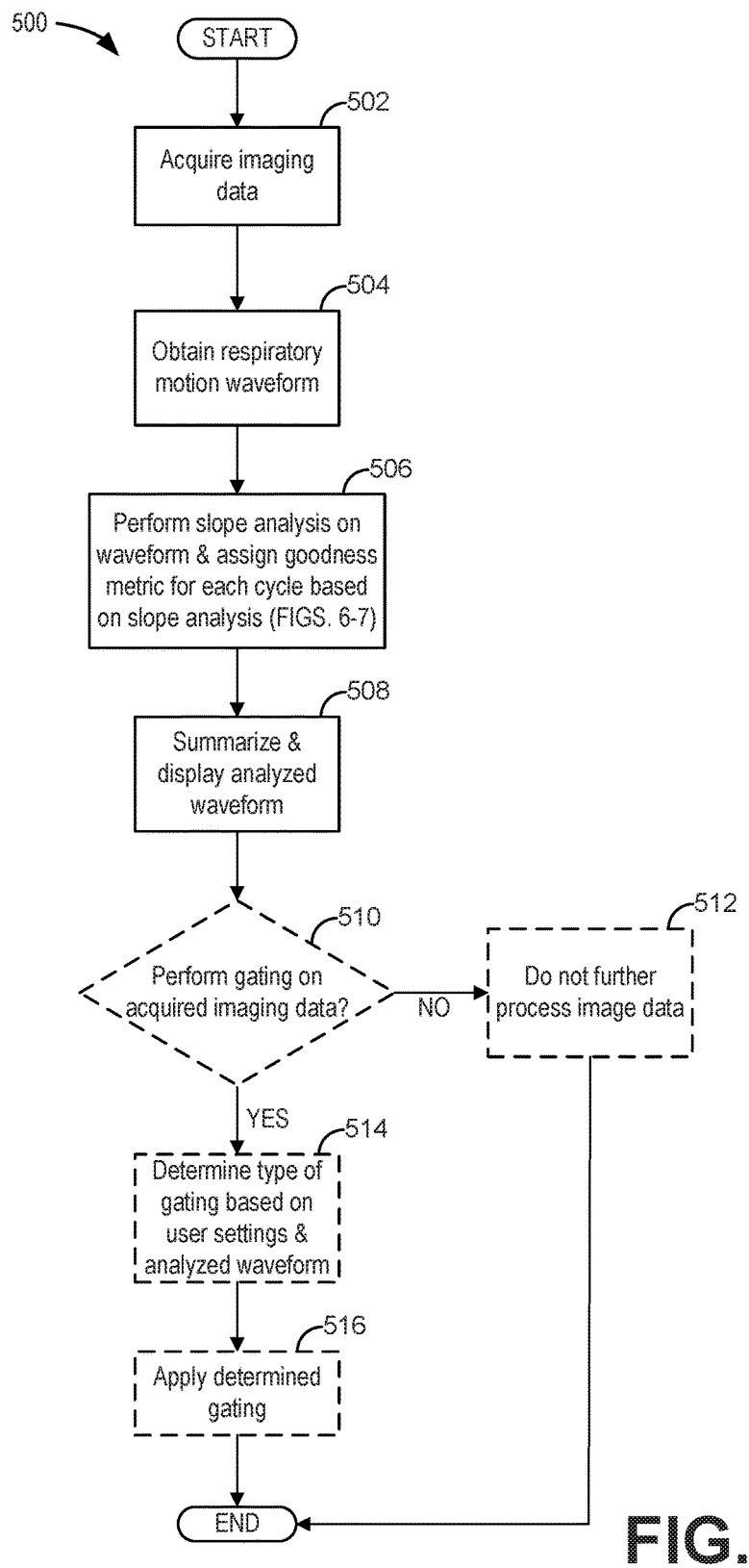
FIG. 5 shows a method for analyzing a respiratory motion waveform acquired during medical imaging and determining how to process acquired image data based on the analyzed respiratory motion waveform according to an embodiment of the invention.
Figure 6:
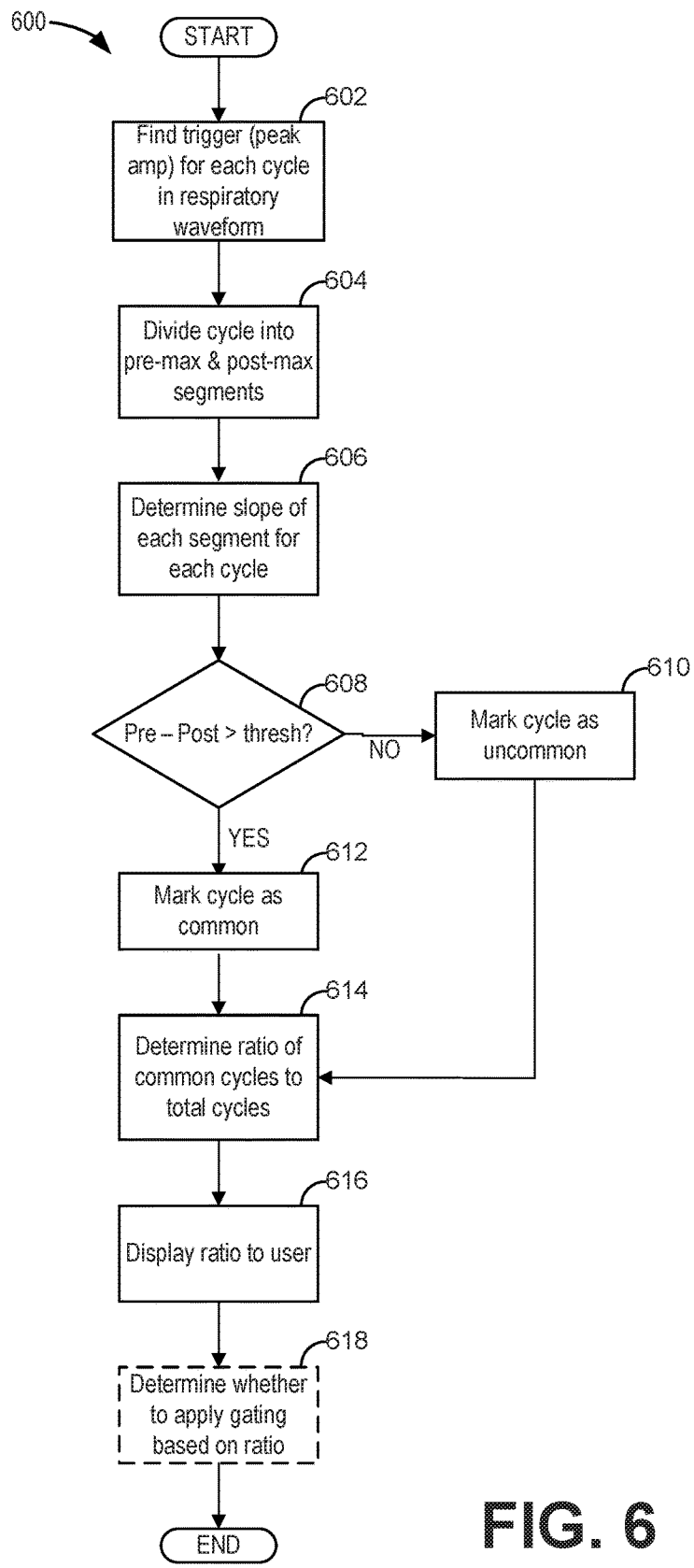
FIG. 6 shows a method for performing a slope analysis on a respiratory motion waveform acquired during medical imaging according to an embodiment of the invention.
Figure 7:
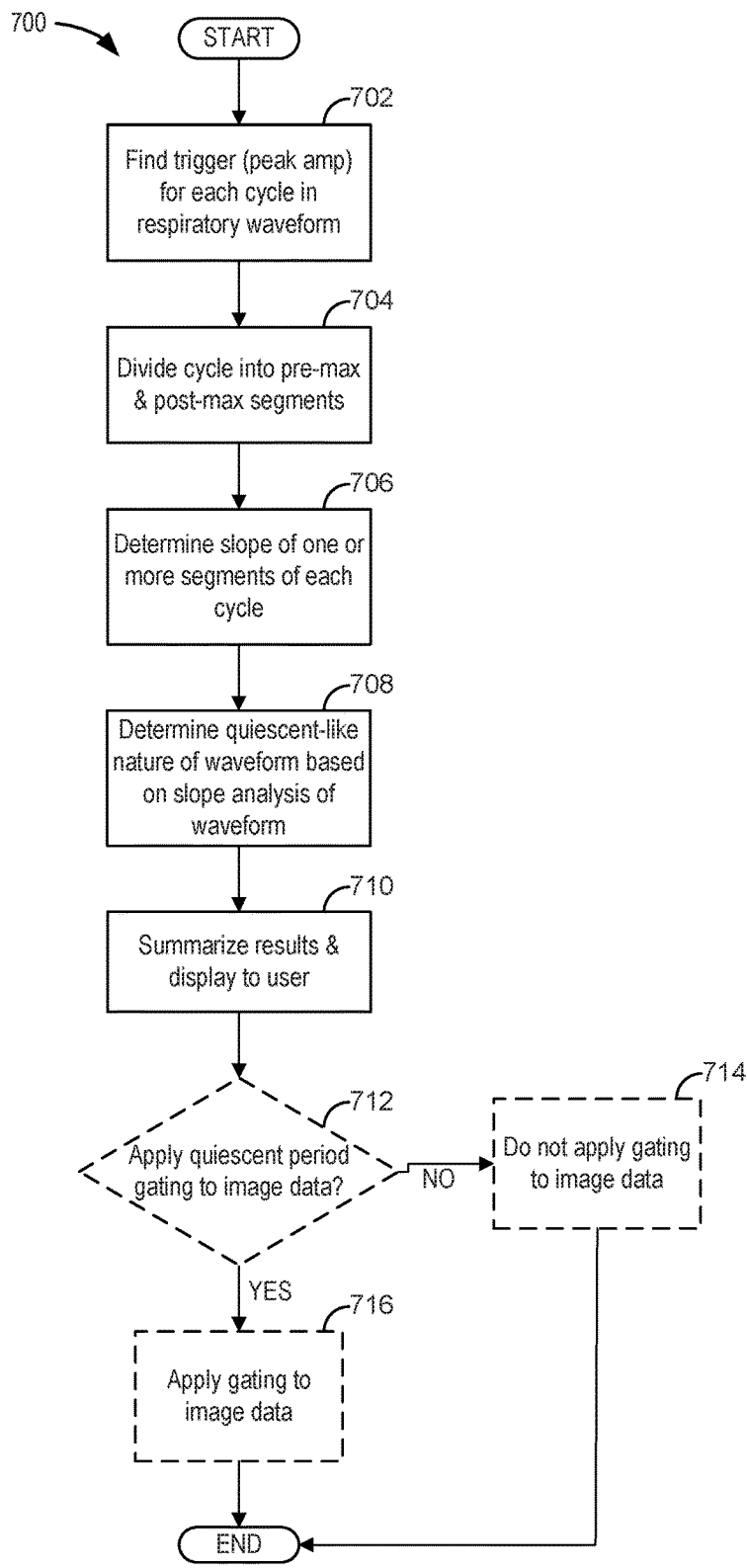
FIG. 7 shows a method for analyzing a quiescent nature of a respiratory motion waveform acquired during medical imaging and determining whether to apply quiescent period gating to acquired image data according to an embodiment of the invention.

The following description relates to various embodiments of processing medical imaging data based on a respiratory motion waveform. In particular, systems and methods are provided for analyzing a respiratory motion waveform acquired during acquiring molecular imaging data with a molecular imaging device, such as the PET scanner shown in FIG. 1. As shown in FIG. 1, molecular imaging data may be acquired from a medical molecular imaging device, such as a PET scanner. The acquired data may be processed and analyzed at a data processing apparatus optionally coupled to the molecular imaging device. A respiratory motion waveform indicative of a patient's breathing pattern during acquisition of the imaging data may be obtained either from a sensor coupled to the patient or derived from the acquired data itself. Example respiratory motion waveforms are shown in FIG. 4. In some examples, the acquired imaging data may be respiratory-gated using the respiratory motion waveform in order to reduce respiratory motion effects that may degrade the image(s) generated from the acquired data. Examples of several gating techniques using the respiratory motion waveform are shown in FIGS. 2 and 3. In some examples, the shape of the respiratory waveform may help to determine whether gating may be applied to the acquired imaging data in order to increase image quality and accuracy for medical diagnosis. A method for analyzing a respiratory motion waveform acquired during medical imaging and determining how to process acquired imaging data based on the analyzed respiratory motion waveform is shown in FIG. 5. In one example, the respiratory waveform may be analyzed by determining a slope before and after each peak in the waveform and comparing these slopes, as shown in FIG. 6. Whether or not to apply a specific quiescent period gating technique to the acquired imaging data may also be based on slopes of the respiratory waveform that are indicative of the quiescent-like nature of the waveform, as shown at FIG. 7. The analysis of the respiratory waveform may be used both for automatic processing and gating decisions for acquired imaging data and for diagnostic purposes. In one example, the results of analyzing the respiratory waveform may be output to a user, such as in the example output shown in FIG. 8, and used for medical diagnosis or to inform further medical procedures.

Though a PET system is described by way of example, it should be understood that the present techniques may also be useful when applied to images acquired using other imaging modalities, such as tomosynthesis, MRI, C-arm angiography, CT, and so forth. The present discussion of a PET imaging modality is provided merely as an example of one suitable imaging modality.

FIG. 1 shows a system 100 for clinical diagnosis of a subject according to an embodiment of the present invention. The system 100 includes a data processing apparatus 120 that comprises various interfaces 123, 126, an image acquisition module 122, and a data analyzer 124. The interfaces 123, 126, image acquisition module 122, and data analyzer 124 can be logically coupled together by way of a data bus 125 under the control of a central processing unit (not shown).

The data processing apparatus 120 provides a first general purpose interface 126 for interfacing the data processing apparatus 120 to external components. In this embodiment, the external components include: an input data link 127 coupled to at least one user input device 128 (e.g. a mouse/keyboard/etc.), a network data link 143 coupled to the Internet 142, and a display data link 129 coupled to a display 130. Additionally, the general purpose interface 126 also provides a GUI 123 through which a user of the system 100 can input data, commands etc., and receive visual information by viewing the display 130.

The GUI 123 may be operable to generate a two- and/or three-dimensional representation of various anatomical portions of the subject. Such representations may, for example, include color coding of regions according to uptake or use of a substance in respective of those regions. This provides ease of visualization for users of the system 100. In addition, in various embodiments, a user can also rotate images and/or slice 3D images by manipulating the GUI 123 using the input device 128. For example the representations may be representations of acquired image data that is then displayed to the user via the display 130. In another example, the GUI 123 may generate a representation of a one-dimensional respiratory waveform and summary statistics for the respiratory waveform for display on the display 130.

In various embodiments, the data processing apparatus 120 can comprise a general purpose computer, such as, for example, a personal computer (PC). Such a general purpose computer can use software modules to provide both the image acquisition module 122 and the data analyzer 124, and hence can be implemented by upgrading the functional capability of existing equipment using software upgrades. For example, a computer program product 144, comprising computer code, may be transmitted from a remote server (not shown) via the Internet 142 to the data processing apparatus 120 through the network data link 143 or may be provided on a physical medium, such as, for example, a CD, DVD, magnetic disk, ROM, flash memory device, etc.

The system 100 also comprises an optional positron emission tomography (PET) scanner 140 coupled to the data processing apparatus 120 by a data link 139, and an optional data store 132 coupled to the data processing apparatus 120 by a data link 131. The PET scanner 140 and/or the data store 132 may be configured to acquire and provide data to the image acquisition module 122. As one example, the data may be referred to herein as pre-image data or imaging data and is defined as data that is acquired with a molecular imaging device (e.g., medical imaging device), such as PET scanner 140, and is then used to create an image for display to a user. For example, where no PET scanner is provided, data could be provided from the data store 132 that may contain previously generated data (acquired from a molecular imaging device) stored therein. Such previously generated data could be generated remotely from the system 100 (e.g. in a remote hospital, etc. where suitable image data generation facilities are available), and subsequently transferred to the data store 132 from where it can be retrieved by the image acquisition module 122. The image acquisition module 122 is further operable to transfer data generated by the PET scanner 140 to the data store 132 for archiving purposes. In alternate embodiments, a different molecular imaging apparatus (other than the PET scanner 140) may be coupled to the data processing apparatus 120 via the data link 139. For example, the different molecular imaging apparatus may include a CT scanner, a MRI apparatus, or the like.

The data analyzer 124 is operable to perform numerical analysis on acquired data. Such data can be provided in the form of a sequence of data frames, corresponding, for example, to a temporal sequence of coincidence events (PET) derived from a certain portion of a subject's anatomy. For example, the data frames may correspond to a time sequence of coincidence events showing the uptake of a radio-isotope tagged molecule in a subject's brain, heart, etc. derived from a PET scan. Alternatively, or in addition, the data frames may be derived from magnetic resonance imaging (MRI) (e.g. from different scan sequences, dynamic studies, and/or functional imaging), optical imaging (e.g. at different wavelengths) and/or X-ray imaging (e.g. when performing a dynamic study, CT-scan etc.). The data analyzer 124 may perform data analysis either in real time, on coincidence data received from the PET scanner 140 or alternate molecular imaging apparatus coupled to the data processing apparatus 120, or perform data analysis on previously acquired and stored data (e.g., data stored in the data store 132).

The system 100 further comprises an optional sensor 133 coupled to the data processing apparatus 120 via either a wireless or wired connection. The optional sensor 133 may be one or more of a marker box, optical sensor, chest strap sensor, or the like, configured to coupled to a patient being scanned by the PET scanner 140 (or other molecular imaging device). The data analyzer 124 may then receive and process the output received from the sensor 133 to further process data or analyze theسنsor data from sensor 133 and display the results to a user via the display 130.

In molecular imaging, such as imaging with the PET scanner 140 shown in FIG. 1, or alternate molecular imaging apparatus (e.g., such as a CT, x-ray, or MRI apparatus), a patient may be imaged for a period of time in order to acquire enough data to form images of a desired tissue or region of interest within the patient. For example, during PET imaging, multiple scan positions may be taken along the length of the patient. Each scan position may result in a scan and acquiring of imaging data for several minutes (e.g., 3 minutes per position). Each scan may occur during several breath cycles of the patient (e.g., several breaths, or cycles of inspiration and expiration). However, respiration of the patient during the scan can cause image blur and quantitation inaccuracy in molecular imaging. To mitigate such effects, the acquired image data can be respiratory-gated (broken into like-displacement bins per respiratory cycle) or only the portion of the data acquired under a more quiescent-like part of the cycle can be kept to form an image. A quiescent-like part of the breath cycle may be defined as a portion of the cycle that has the flattest amplitude compared to the rest of the cycle (e.g., having a slope lower than a threshold). For example, a quiescent-like respiratory waveform follows the pattern of a quick intake of air, similar exhale, and a pause (the quiescent portion) before another inhalation. Gated imaging data can be subsequently motion corrected using global non-rigid registration techniques.

The respiratory waveform indicative of a patient's respiratory motion during a molecular imaging scan (e.g., data acquisition) may be obtained either from a separate sensor (such as sensor 133 shown in FIG. 1) or data processing of the acquired imaging data (e.g., using a data processing apparatus, such as apparatus 120 shown in FIG. 1). In one embodiment, a temporal list of the acquired coincidence data may be obtained. The temporal list of data includes spatial information of the acquired event-by-event data. The resulting waveform may be a one-dimensional waveform of amplitude vs. time and obtaining such a waveform from the acquired imaging data may be referred to herein as principal component analysis (PCA). In another embodiment, the 1-D respiratory motion waveform may be obtained from an external sensor (e.g., external to the molecular imaging apparatus) coupled to the patient being scanned and not from the acquired imaging data. For example, as explained above with reference to sensor 133 in FIG. 1, the sensor may be a marker box or chest strap coupled to the patient which tracks the respiratory motion of the patient over time (e.g., spatial data, or amplitude, over time). In both embodiments, the resulting 1-D respiratory motion waveform correlates to image data acquired over the same time period and is thus used to determine the gating to be applied to the acquired data. Examples of respiratory waveforms acquired either using PCA or a separate sensor coupled to the patient are shown in FIGS. 2-4, as explained further below.

FIG. 2 shows an example of typical (e.g., standard) gating (binning) technique that may be applied to imaging data acquired with a medical imaging device (such as a PET scanner). Specifically, FIG. 2 shows a graph 200 of how a one-dimensional respiratory motion waveform may be temporally divided at regular intervals into "bins", referred to herein as gating or binning, in order to reconstruct PET images with reduced motion blur. Molecular imaging data acquired within each temporal bin may then be post-processed together, in order to construct a final image and/or images within each respective bin, as discussed further below.

Graph 200 shows a patient's respiratory motion, depicted as line 206, comprising respiratory cycles wherein the global minima of each respiratory cycle is marked as line 202, which defines the beginning of a new respiratory cycle and the end of the immediately preceding respiratory cycle. Respiratory cycles along line 206 may be further divided in a regulated, temporally consistent manner into a plurality of bins, depicted in FIG. 2 as lines 204. The number of bins used for all the data within a scan may vary, depending on a number of variables such as duration between respiratory cycles, operating conditions of the imaging system being used, medical professional preferences, etc. Moreover, it will be appreciated that a patient's breathing may include irregularities leading to respiratory cycles that vary in temporal duration. As such, while each respiratory cycle along line 206 may be divided into the same number of bins (e.g., six bins), the size/duration of the bins (as depicted by a distance between adjacent lines 204) may vary from cycle to cycle. For example, looking at FIG. 2, it may be seen that a first (as defined by time, along the x-axis) complete respiratory cycle along line 206 is slightly shorter in duration than the following complete cycle, and as such, each bin in the first cycle lasts for a shorter period of time than each bin in the following cycle of line 206. In this way, for FIG. 2, the spatial information (as defined by amplitude) of a patient's respiratory cycle (as defined by line 206) may be temporally plotted, from a temporal list, to generate a series of divided respiratory cycles comprising an identical number of bins per cycle. It will be appreciated that the same temporal list used to generate graph 200 may also include acquired image data, so that the images acquired during a molecular imaging session are temporally linked to spatial data, meaning that the temporal divisions applied to the respiratory cycles along line 206 may also be applied to any data acquired during the same time frame.

Looking at FIG. 2, each complete respiratory cycle along line 206 is divided by lines 202 and 204 into six bins (labelled 1-6, above the x-axis), with a corresponding bin of images (e.g., molecular imaging data) for each bin along line 206. That is to say, once the respiratory cycles along line 206 have been divided into an equal number of bins (e.g., six bins), the data acquired within a period of time corresponding to each bin of a respiratory cycle may then be combined with data from the corresponding bin of all other respiratory cycles along line 206 for the one-dimensional waveform. The data of each bin may then be post-processed together, to form a composite image(s), yielding a final image(s) with reduced motion induced blur. In FIG. 2, there are six bins labelled Bin 1 208, Bin 2 210, Bin 3 212, Bin 4 214, Bin 5 216 and Bin 6 218, wherein each of Bin 1-6, 208-218, is comprised of data acquired during the corresponding bin of the respiratory cycle along line 206. For example, looking at Bin 1 208 of FIG. 2 it may be seen that a composite image is produced from data acquired from the same bin (i.e., bin "1" as seen in FIG. 2) across multiple respiratory cycles along line 206, as indicated by the two lines diverging from the top of Bin 1 208, towards the two corresponding bin "1"s of line 206. Similarly, looking at Bin 2 210 of FIG. 2, it may be seen that a composite image is generated from data acquired during the second bin (i.e., bin "2" as seen in FIG. 2) of each complete respiratory cycle along line 206. It will be appreciated that the composite images of Bins 3-6, 212-218 are generated in the same manner as that described above for Bin 1 208 and Bin 2 210.

In this way, binning may be applied using a one-dimensional wave form, in order to firstly divide the waveform into respiratory cycles with identical start/end points, to secondarily divide the respiratory cycles into an identical number of bins with identical durations per bin per cycle, and lastly, to generate an image with reduced blur for each corresponding bin, across all complete respiratory cycles of the one-dimensional wave form.

FIG. 3 shows an example of a quiescent period gating (e.g., binning) technique that may be applied to imaging data acquired with a medical imaging device (such as a PET scanner). Quiescent period gating may be most effective when the respiratory motion waveform has a consistent quiescent period over many cycles. Otherwise, applying this gating technique may not significantly reduce image blur due to respiratory motion effects and may also increase image noise due to the deletion of certain portions of the acquired image data.

FIG. 3 shows a respiratory motion waveform 302 acquired during acquisition of imaging data (e.g., during a PET scan). The respiratory motion waveform 302 includes several breath cycles. Triggers for each cycle are set at each peak 304 (maximum amplitude) in the respiratory motion waveform 302. The cycle segments between each peak 304 are broken up into three segments. The first segment 306 is a first 30% of the waveform cycle after the peak. The second segment 308 is a middle 50% of the waveform cycle and the third segment 310 is a final 20% of the waveform cycle before the next peak. For quiescent period gating, only the acquired data (e.g., imaging data) taken during and corresponding to the second segment 308 of each cycle of the respiratory waveform is kept and the remaining portions of the data are discarded. This kept data is then used to generate a final image of the scanned tissue. It may be said that only the data taken during the most quiescent (e.g., flat) portion of the respiratory waveform is kept and used to form an image. The resulting image may then have less image degradation due to respiratory motion effects. It should be realized that the length of the segments 306, 308 and 310 can be parameterized and changed based upon the waveform, imaging protocol, or other factors.

Though respiratory gating techniques may be useful for improving image quality, not all patient breathing patterns are the same, or consistent. Different types of gating (also referred to herein as binning) or discarding a portion of the acquired image data may only be advantageous for certain breathing patterns, such as patterns that are consistent over multiple breath cycles and/or have a consistent quiescent period. Analyzing a shape of a respiratory waveform acquired during acquisition of molecular imaging data may help to inform a user about a patient's breathing pattern and/or be used to determine how best to process acquired data to reduce respiratory motion (e.g., whether to apply gating, discard a portion of the data, or do nothing).

FIGS. 5-7 show example methods for obtaining and analyzing a respiratory waveform (e.g., respiratory motion waveform) acquired during acquiring imaging data with a molecular imaging apparatus (e.g., such as PET scanner 140 shown in FIG. 1). FIG. 4 shows example respiratory waveforms analyzed using the methods presented at FIGS. 5-7. The methods described herein may be performed by a processor, such as data processing apparatus 120 shown in FIG. 1. In one example, the processor may be coupled to the molecular imaging apparatus and may process the acquired data in real-time or after data acquisition in complete. In another example, the processor may post-process already acquired imaging data stored in a memory (e.g., storage device including a non-transitory memory) of the processor. The methods described herein may be executed by the processor in conjunction with the systems described herein (e.g., data store, PET scanner, display, user inputs, or the like) according to instructions stored in a non-transitory memory of the processor.

Turning first to FIG. 5, a method 500 is shown for analyzing an acquired respiratory motion waveform and determining how to process data acquired with a molecular imaging device (e.g., acquired imaging data) to reduce respiratory motion effects based on the analyzed respiratory waveform. Method 500 begins at 502 by acquiring imaging data. In one example, acquiring imaging data may include acquiring data in real-time from a molecular imaging apparatus coupled to the processor (e.g., such as PET scanner 140 shown in FIG. 1, or an alternate molecular imaging apparatus such as a CT, MRI, or x-ray apparatus). As such, the acquired data may include one or more scans of a region or tissue of interest of a patient. The acquired data may include a temporal list of data that may be used to generate one or more images of the scanned tissue. Additionally, acquiring data may include acquiring data for a set duration of time (e.g., 3-4 minutes) for one or more scan positions. In another example, acquiring imaging data at 502 may include accessing previously acquired imaging data stored in a memory of the processor and/or a data store (such as data store 132 shown in FIG. 1) coupled to the processor (e.g., data processing apparatus 120 shown in FIG. 1). As such, the acquiring imaging data may be performed in real-time during scanning of a patient or during a post-processing session.

At 504, the method includes obtaining a respiratory motion waveform. As described above, the respiratory motion waveform is a one-dimensional waveform of the respiratory motion of patient (e.g., spatial data, such as amplitude) over time, acquired during the acquiring of the imaging data at 502. As such, the time scale of the obtained respiratory motion waveform may correlate to the time scale of the acquired imaging data (e.g., such that specific image slices correlate to specific respiratory motion at a certain segment of time). In one example, the respiratory motion waveform may be obtained directly from the acquired imaging data, using the principal component analysis (PCA) technique described above. As such, the respiratory motion waveform is obtained from a temporal list of acquired imaging data. In another example, the respiratory motion waveform is obtained from a sensor coupled to the patient being scanned during the acquiring of the imaging data (e.g., such as sensor 133 shown in FIG. 1). As described above, the sensor may include a marker box, optical sensor, a position sensor, or the like coupled to the patient in order to measure the respiratory motion of the patient during the imaging scan. In one example, the resulting respiratory motion waveform may resemble one of the example respiratory waveforms 404 or 414 shown in FIG. 4.

At 506, the method includes performing a slope analysis on the obtained respiratory motion waveform and assigning a goodness metric for each cycle of the respiratory motion waveform based on the slope analysis. As described above, each respiratory waveform includes a plurality of cycles (e.g., breath cycles), where each cycle includes an inspiration (increase in amplitude) and expiration (decrease in amplitude). Each cycle of the respiratory waveform may be measured from set positions in the cycle (e.g., peak to peak or valley to valley). In one example, as shown in graphs 400 and 402 in FIG. 4, each cycle may be measured from a first valley (e.g., minimum amplitude), as indicated at 416, to the next valley (e.g., next minimum amplitude), as indicated at 418, and each cycle may then include a peak (e.g., maximum amplitude for the cycle), as indicated at 417.

Returning to FIG. 5, the slope analysis may include estimating the slope of the waveform (e.g., velocity or derivative of the amplitude waveform) at various points in the cycle. In one example, as explained further below with reference to FIGS. 6 and 7, a pre-max (e.g., before the peak) and post-max (e.g., after the peak) slope may be determined for each cycle and compared to one another. As one example, the goodness metric may be an indication of how closely the pre-max and post-max slopes match, whether the pre-max slope is greater than the post-max slope, and/or whether the pre-max and post-max slopes match a desired or common respiratory waveform. The assigned goodness metric may inform a user of a degree of consistency of the respiratory waveform (e.g., how alike each cycle is) and/or the quiescent-like nature of the respiratory waveform (e.g., if the waveform has a consistent flat portion after each expiration and before a subsequent inhalation).

At 508, the method includes summarizing and displaying the respiratory motion waveform analyzed at 506. As one example, the method at 508 may include generating an output, such as the example output shown in FIG. 8, and displaying the generated output to the user.

Figure 8:
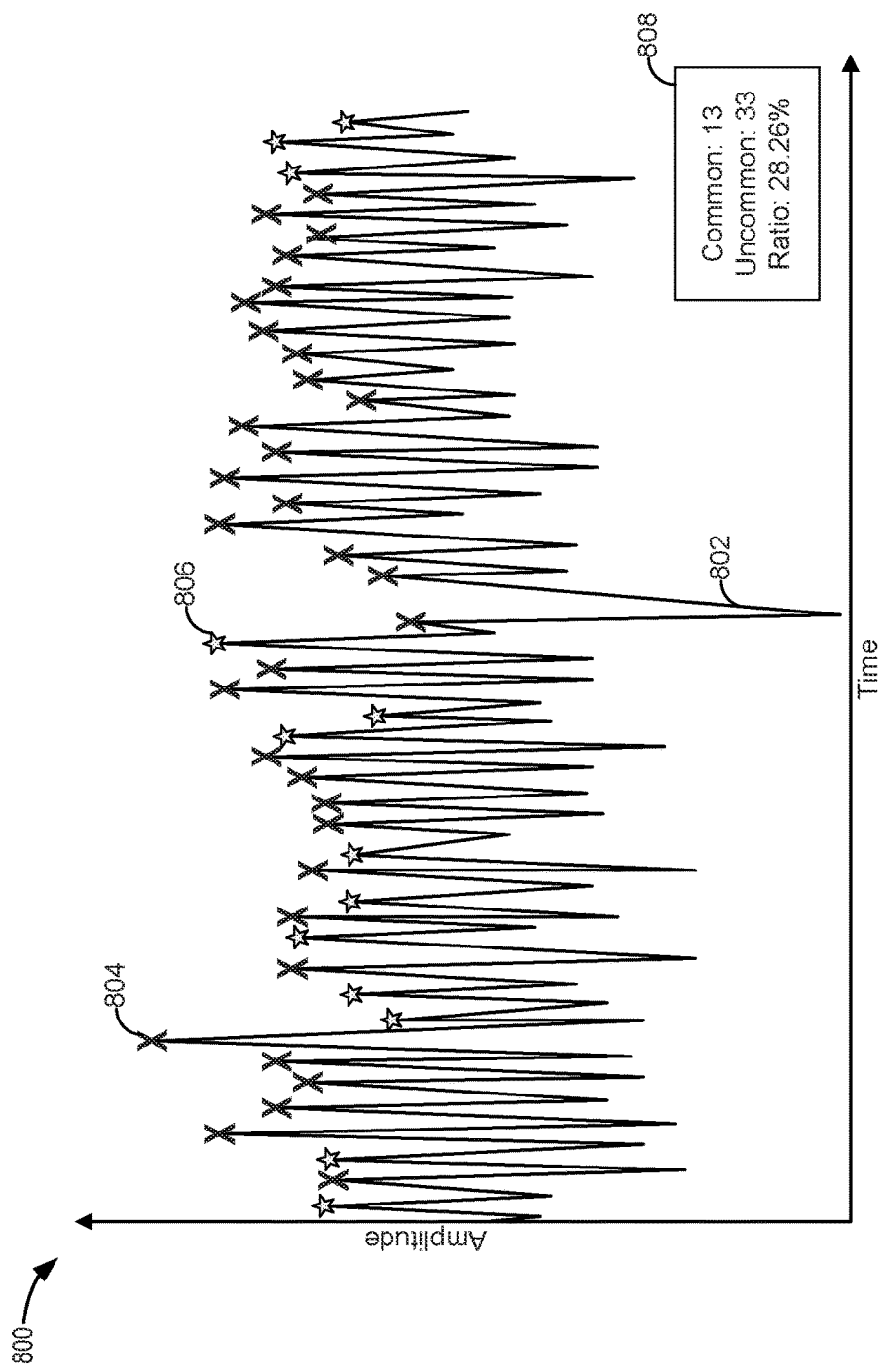
FIG. 8 shows an example output displayed to a user for an analyzed respiratory motion waveform acquired during medical imaging according to an embodiment of the invention.

As shown in FIG. 8, the generated output may include a graph 800 of the respiratory waveform (amplitude on y-axis and time on x-axis). As shown in FIG. 8, the graph 800 may be of a smoothed (e.g., filtered or smoothed via various smoothing techniques, as described further below) respiratory motion waveform 802. However, in alternate embodiments, the graph 800 may additionally or alternatively include the raw respiratory motion waveform. The displayed graph may optionally include pre-max and/or post-max slope lines drawn on the waveform (not shown in FIG. 8) and/or symbols over each cycle indicating the assigned goodness metric (e.g., a star 806 or X 804, as shown in FIG. 8). The graph may also optionally include color coding corresponding to the assigned goodness metric for each cycle. In another example, as shown in FIG. 8, the output may also include a data output 808 displaying statistics from the respiratory waveform slope analysis.

As shown in FIG. 8, the data output 808 includes an indication of the number of common cycles (cycles marked with stars 806, as described further below), a number of uncommon cycles (marked with X's 804, as described further below), and a ratio of a number of common cycles to total cycles of the respiratory waveform. In another embodiment, the data output 808 may include one or more of slope data (e.g., pre-max slope, post-max slope, instantaneous slope values, average slope values for designation portions of the cycle, or the like), a number of common cycles (e.g., cycles meeting certain thresholds or goodness metrics, as described further below), a number of uncommon cycles, and/or a ratio of common to total cycles. The data output 808 may also include data and/or an indicator indicating the quiescent-like nature of the respiratory motion waveform (e.g., a percentage or other measure of how quiescent or consistently quiescent the respiratory motion waveform is). The data output 808 may alternatively or additionally include respiratory health data for the patient and/or a suggested gating technique for further processing the acquired imaging data (e.g., a certain gating technique, quiescent period gating, keeping a certain percentage of the data, keeping only the indicated common cycles, or performing no additional processing on the acquired image data).

Returning to FIG. 5, in some examples, a health professional may use the displayed output at 508 as a diagnostic for analyzing a patient's respiratory health and/or dictating further medical testing or procedures. As such, in some examples, the method may end at 508. However, in alternate embodiments, the analyzed respiratory motion waveform may be used to determine whether further processing of the acquired data may be advantageous (e.g., whether gating or eliminating some of the acquired image data may result in higher quality images for more accurate medical diagnosis). In this embodiment, the method may continue to 510. In FIG. 5, the methods at 510, 512, 514, and 516 are dashed to indicate optional methods depending on the embodiment.

At 510, the method includes determining whether or not to perform gating on the acquired imaging data. As explained above, gating (binning) or discarding a portion of the acquired imaging data may be performed in order to reduce the effects of respiratory motion. However, under some circumstances, gating techniques may not be beneficial (e.g., if the cycles of the respiratory waveform are not consistent, or if the pre-max (pre-peak) and post-max (post-peak) slopes of the respiratory cycles differ too much from one another). Additionally, in some instances, discarding portions of the acquired imaging data to reduce respiratory motion effects may increase the noise of the acquired data and resulting generated image. Thus, there may be a trade-off between discarding acquired imaging data for reducing respiratory motion effects and keeping imaging data to reduce image noise. The method at 510 is explained in further detail below with reference to FIGS. 6 and 7. In one example, the method at 510 may include comparing the pre-max and post-max slope of each respiratory cycle in the respiratory waveform and determining how consistent the cycles of the respiratory waveform are based on the comparison. If the shape of the respiratory waveform is relatively consistent (e.g., a ratio of common cycles to total cycles, as determined from the slope analysis is greater than a threshold), the processor may determine that a gating technique may be applied to the acquired data. In another example, the method at 510 may include determining a quiescent-like nature of the respiratory waveform (as shown in FIG. 7) and applying quiescent period gating (also referred to as binning) to the acquired data if slope analysis indicates that enough cycles in the respiratory waveform have a significant duration of the quiescent period.

If the method at 510 determines that respiratory gating (or discarding of a portion of the acquired data) should not be applied to the acquired data, the method proceeds to 512 to no further process the acquired image data. As a result, the method at 512 may include generating an image from the acquired image data and displaying the generated image to a user. Alternatively, if the method at 510 determines that gating should be applied to the acquired imaging data, the method continues to 514 to determine the type of gating to perform based on user settings and/or the analyzed respiratory motion waveform (e.g., based on the slope analysis at 506). The method at 514 may be performed automatically by the processor based on the analyzed respiratory motion waveform and/or user settings. For example, the method at 514 may include determining the type of gating based on the determined slopes (e.g., pre-max slope, post-max slope, average slope, a quiescent period slope, a slope for a percentage of the post-max (post-peak amplitude) portion of each cycle) for each cycle of the respiratory waveform. In one example, if the ratio of common cycles to total cycles of the respiratory waveform (as determined at 614 in method 600, as described further below with reference to FIG. 6) is greater than a threshold (e.g., 60%), the processor may decide to apply a typical gating technique (e.g., such as the gating technique shown in FIG. 2) to the acquired imaging data. In another example, if the slope analysis indicates that a threshold number of cycles of the respiratory waveform has a quiescent period (as indicated by a post-max slope or a slope of a portion of the post-max portion of the cycle, for example) then the processor may decide to apply a quiescent period gating technique (e.g., such as the quiescent period gating technique shown in FIG. 3) to the acquired imaging data. In another example, the slope analysis may include an offset from a reference point in the cycle (e.g. at peak inspiration) from which to perform the slope analysis for comparison over multiple cycles. Finally, the slope analysis may be performed on several equal increments of each cycle and compared increment-wise over multiple cycles to determine a consistency metric for deciding whether to perform standard (multi-bin) gating on the data (for example, the type of gating shown in FIG. 2). For example, the more similar slopes are over several cycles for each increment (or segment), the more beneficially applying the standard gating would be.

Additionally, one or more user settings may at least partially dictate which type of gating to apply to the acquired image data. For example, a user may select a preferred gating technique based on their knowledge of the patient, type of tissue being scanned, or type of scanning method (e.g., PET, MRI, or CT). In another example, the processor may automatically determine a preferred gating technique based on received user inputs of the scanning method, type of tissue being scanned, and/or patient type (e.g., age, health, disease states, sex, or the like). In one example, the processor may then decide which type of gating to apply based on both the user settings and the analyzed respiratory motion waveform. In another example, the processor may decide whether or not to apply the preferred gating technique (as determined from user settings) based on the analyzed respiratory waveform.

At 516, the method includes applying the determined gating technique to the acquired imaging data. In some examples, the method at 516 may further include acquiring additional data with the molecular imaging device if a certain number of cycles or percentage of the already acquired data is discarded. This may occur if the acquired data is being analyzed in real-time. In another example, the method at 516 may include generating and displaying one or more images based on the gated imaging data.

In some examples, if method 500 is being executed by a processor coupled to a molecular imaging device (e.g., such as a medical imaging device such as a PET, MRI, CT, or x-ray device), method 500 may proceed automatically in its entirety (from 502-516) without additional user input. For example, gating may be automatically applied to the acquired imaging data based on the analyzed respiratory waveform, as analyzed during method 500. As such, gating decisions and applications may proceed automatically during an imaging procedure. This may reduce the time to generate a final image output while increasing the accuracy of the generated image. Additionally, automating this process may increase ease of use for the user and allow a greater number of medical professionals to execute the scan and/or image generation procedure.

Turning now to FIG. 6, a method 600 for performing a slope analysis on a respiratory motion waveform acquired during medical imaging (such as the respiratory waveform acquired during method 500 presented at FIG. 5) is shown. Method 500 may continue from and/or be part of method 600, as described above. As such method 600 includes analyzing the respiratory motion waveform acquired during acquiring imaging data and determining whether to apply gating to the acquired imaging data. Method 600 begins at 602 (which may proceed from method 506 shown in FIG. 5) by finding a trigger for each cycle in the respiratory motion waveform. A trigger may be defined as a common point within each cycle of the respiratory waveform. As one example, as shown in FIG. 4, the trigger may be the peak (e.g., maximum) amplitude (shown at 417) of each cycle in the respiratory waveform. The peak amplitude indicates the transition from inspiration to expiration within the respiratory cycle. As a result, each cycle may be defined between adjacent valleys (e.g., minimum amplitudes 416 and 418 shown in FIG. 4) in the respiratory waveform such that each cycle includes a peak and the end of one cycle is the beginning of the next. The method at 602 may optionally include applying smoothing to the respiratory waveform to reduce noise. Plots 410 and 420 in FIG. 4 show an example of a smoothed respiratory waveform. As one example, a rolling average smoothing function may be applied to the respiratory waveform.

At 604, the method includes dividing each cycle into pre-maximum (e.g., pre-max or pre-peak) and post-maximum (e.g., post-max or post-peak) segments, where the pre-max segment occurs before the peak amplitude and the post-max segment occurs after the peak amplitude of each cycle. For example, FIG. 4 shows a pre-max segment 406 and post-max segment 408 of one cycle of a respiratory waveform 404 or 414. The method at 604 may optionally include applying a condition of monotonicity to the respiratory motion waveform in order to remove small/short bumps in the waveform. Plots 410 and 420 in FIG. 4 show examples of respiratory waveforms where a condition of monotonicity has been applied.

At 606, the method includes determining a slope of each of the pre-max and post-max segments of each cycle in the respiratory waveform. In this example, the slope may be the velocity of each segment (e.g., the time derivative of the designated segment of the amplitude waveform). As one example, the determined slopes may be of the raw respiratory waveform (e.g., plots 404 and 414 shown in FIG. 4). As another example, the determined slopes may be of the corrected/smoothed respiratory waveform (e.g., plots 410 and 420 shown in FIG. 4).

At 608, the method includes determining, for each cycle, if a difference between the determined pre-max slope and post-max slope is greater than a threshold. In one example, the threshold may be zero such that when the difference between the pre-max and post-max slopes is greater than zero, the pre-max slope is greater than the post-max slope. In another example, the threshold may be a different positive value such that the method includes determining whether the pre-max slope is greater than the post-max slope by a threshold amount (e.g., the threshold). In one example, the threshold used at 608 may be a pre-set threshold (e.g., such as zero or some other positive value). As another example, the threshold used at 608 may be a configurable value that may be automatically adjusted by the processor based on the acquired image data and/or one or more user inputs. In another example, the threshold used at 608 may be manually selected (e.g., input) by the user. If the difference between the pre-max slope and the post-max slope for a single cycle of the respiratory waveform is not greater than the set threshold, the method continues to 610 to mark that cycle as uncommon (e.g., not like the rest). Marking the cycle as uncommon may also be referred to herein as marking the cycle with a second designation. Marking the cycle as uncommon (or with the second designation) may include adding an indicator (e.g., X) to a displayed graph of the respiratory waveform (as shown at 422 in graph 402 of FIG. 4). Marking the cycle as uncommon may additionally or alternatively include adding a count to an uncommon cycle counter for the respiratory waveform. As such, the processor may keep track of how many cycles within the respiratory waveform are marked as uncommon.

Alternatively, if the difference between the pre-max slope and the post-max slope for a single cycle of the respiratory waveform is greater than the set threshold, the method continues to 612 to mark that cycle as common. Marking the cycle as common may also be referred to herein as marking the cycle with a first designation, different than the second designation. Marking the cycle as common may include adding an indicator (e.g., star) to a displayed graph of the respiratory waveform (as shown at 412 in graph 400 of FIG. 4). Marking the cycle as common may additionally or alternatively include adding a count to a common cycle counter for the respiratory waveform. As such, the processor may keep track of how many cycles within the respiratory waveform are marked as common.

At 614, the method includes determining a ratio of the number of common cycles to total cycles in the respiratory waveform. This ratio may be reflected as a percentage of common cycles to total cycles within the respiratory waveform. It should be noted that the methods at 604-612 are repeated for each individual cycle of the obtained respiratory motion waveform.

The method then continues to 616 to display to a user (e.g., via a display such as display 130 shown in FIG. 1) the determined ratio. The method at 616 may further include displaying the analyzed respiratory waveform and/or the slope data for the analyzed respiratory waveform. As explained above, FIG. 8 shows an example output displayed to a user which shows the analyzed respiratory waveform with marked common and uncommon triggers (stars and X's, respectively). The displayed waveform may include one or more of the raw respiratory waveform and the smoothed waveform. The displayed slope data may include one or more of the pre-max and post-max slope (e.g., instantaneous velocities for each pre-max and post-max segment) for each cycle of the respiratory waveform, an average pre-max slope and average post-max slope for all cycles of the respiratory waveform, and an average pre-max slope for the pre-max segment of each cycle of the respiratory waveform and average post-max slope for the post-max segment of each cycle of the respiratory waveform. A user may then use the data displayed at 616 for diagnostic purposes.

The method may optionally proceed to 618 to determine whether to apply gating based on the determined ratio (as introduced above at 510 in method 500). For example, the method at 618 may include automatically applying gating to the acquired image data when the determined ratio (as determined 614) is greater than a threshold ratio (e.g., such as 70%). If the ratio of common to total cycles in the respiratory waveform is not greater than the threshold (indicating the respiratory waveform is not consistent enough for gating the image data to be effective), the method at 618 may include not applying gating to the acquired data and instead generating an image from the totality of acquired imaging data and displaying the generated image to the user. For example, not applying gating may include not discarding any of the acquired imaging data based on the respiratory waveform (e.g., not discarding everything but data that was taken during a more quiescent period of the respiratory waveform). Not applying gating may further include not binning the acquired imaging data based on a segmented (binned) respiratory waveform. Instead, all the imaging data may be post-processed together (instead of post-processing by bins to for composite images) and used to form a final image. A further embodiment includes the rejection of data acquired during the cycles marked as uncommon, leaving only the most consistent data for further processing toward making a final image.

In another embodiment, the method at 618 may also include (if occurring in real-time during data acquisition) determining whether further imaging data needs to be acquired (e.g., via additional scans or scan time) to decrease noise (due to deleting/omitting data corresponding to the uncommon respiratory cycles or non-quiescent portions of respiratory cycles) in the acquired data. If it is determined that further imaging data is needed, the method at 618 may include automatically acquiring additional data and adding it to the already acquired data before generating an image based on the additionally acquired and originally acquired data.

FIG. 7 shows a method 700 for analyzing a quiescent-like nature of the respiratory waveform obtained in method 500 and determining whether to apply quiescent period gating to the acquired imaging data (acquired at 502 in method 500). Method 700 may be performed in place of or in addition to the method presented at FIG. 6 based on user or system settings (e.g., based on a preferred or selected gating method). Additionally, method 700 may proceed from 506 presented at FIG. 5.

At 702, method 700 begins by finding a trigger for each cycle in the respiratory motion waveform. As explained above, a trigger may be defined as a common point within each cycle of the respiratory waveform. As one example (as shown in FIG. 4), the trigger may be the peak (e.g., maximum) amplitude of each cycle in the respiratory waveform. The peak amplitude indicates the transition from inspiration to expiration within the respiratory cycle. As a result, each cycle may be defined between adjacent valleys (e.g., minimum amplitudes) in the respiratory waveform such that each cycle includes a peak and the end of one cycle is the beginning of the next. The method at 702 may optionally include applying smoothing to the respiratory waveform to reduce noise. As one example, a rolling average smoothing function may be applied to the respiratory waveform.

At 704, the method includes dividing each cycle into pre-maximum (e.g., pre-max or pre-peak) and post-maximum (e.g., post-max or post-peak) segments, where the pre-max segment occurs before the peak amplitude and the post-max segment occurs after the peak amplitude of each cycle. The method at 704 may optionally include applying a condition of monotonicity to the respiratory motion waveform in order to remove small/short bumps in the waveform. The method at 704 may optionally include use of an offset after the peak (max) prior to calculating the slope of the post-max segment. The additional information when using an offset may be independent of or in conjunction with the previously described pre/post-max comparison and can be used to determine a refined consistency of a quiescent period across cycles.

At 706, the method includes determining the slope of one or more segments of each cycle of the respiratory waveform. This may include performing a per-cycle slope analysis of the pre-max and post-max segments of the respiratory waveform. In a first example, the method at 706 may include determining the instantaneous slope (e.g., velocity) within the post-max segment of each cycle of the respiratory waveform. In a second example, the method at 706 may additionally or alternatively include determining the average waveform slope during a last fraction of the cycle and comparing this to the slope during a first fraction of cycle. For example, the average waveform slope may be determined for the last 40% of each cycle and the first 60% of each cycle or as pre-set percentages including an offset from a pre-determined reference point (e.g., the maximum). As one example, this comparison may be performed using only data from the post-max part of each cycle. In a third example, the method at 706 may additionally or alternatively include determining both the pre-max slope and post-max slope for each cycle and then determining the total fractional cycle time that each of these slopes exceeds a pre-determined threshold. In a fourth example, the method at 706 may additionally or alternatively include splitting the per-cycle data in half based on instantaneous slope and then determining the average slope of the data in the two halves. The method may then include determining an average ratio of the low-slope data (e.g., the half of the data that has a smaller slope) to high-slope data (e.g., the half of the data that has a higher slope).

The method then continues to 708 to determine the quiescent-like nature of the respiratory motion waveform based on the slope analysis performed at 706. As the quiescent-like nature of the respiratory waveform increases, the likelihood of the effectiveness of applying a quiescent period gating to the acquired imaging data increases. In the second example of 706, the average waveform slope during a last fraction of each cycle (e.g., last 40% of each slope) may be the average quiescent-period slope for the entire respiratory waveform. As one example, this average quiescent-period slope and its standard deviation may be indicative of the quiescent-like nature of the respiratory waveform. For example, the smaller the average quiescent-period slope, the more quiescent-like the respiratory waveform. Additionally, the smaller the standard deviation of this average slope, the more consistent the respiratory waveform. In the third example of 706, the total fractional cycle time that each of the pre-max and post-max slopes exceeds the pre-determined threshold is indicative of the quiescent-like nature of the waveform. For example, as the total fractional cycle time that each of the pre-max and post-max slopes exceeds the pre-determined threshold decreases, the more quiescent-like the respiratory waveform. In the fourth example of 706, the smaller the average ratio of the low-slope data to high-slope data, the more quiescent-like the respiratory motion waveform (e.g., the breathing pattern). Additionally, the standard deviation of the constant low velocity portion of the respiratory waveform may be indicative of the potential gain of applying a quiescent period gating to the acquired data corresponding to this portion of the respiratory waveform.

At 710, the method includes summarizing the results of the slope analysis and quiescent-like nature determinations performed at 706 and 708 and displaying this summary to a user (e.g., via a display, such as display 130 shown in FIG. 1). The method at 710 may be similar to the method described above at 508. Further, one example output that may be generated and displayed at 710 is shown in FIG. 8. The method at 710 may include summarizing and displaying any or all of the slope values, standard deviations of average values, and quiescent-like metrics (e.g., a percentage indicating the quiescent-like nature based on the slope analysis) described above with reference to the methods at 706 and 708. In one embodiment, the method may end after 710. In another embodiment, the method may continue to 712.

At 712, the method includes determining whether to apply quiescent period gating to the acquired image data. An example of quiescent period gating is shown in FIG. 3, as described above. The determination at 712 may be based on the quiescent-like nature of the respiratory waveform, as determined at 708 (e.g., if the quiescent-like nature of the waveform is greater than a threshold percentage, as measured by the slope analysis described above and further below). For example, if certain slopes or ratios described above at 706 and 708 (which are indicative of the quiescent-like nature of the respiratory waveform) are above or below certain thresholds, the processor may determine to apply quiescent period gating to the acquired medical imaging data. In some examples, multiple of the slope values or parameters described above at 706 and 708 may be used to determine the quiescent-like nature of the waveform. If one or more of these values meets a threshold, thereby indicating that applying quiescent period gating could be effective, the processor may decide to apply quiescent period gating to the acquired image data. For example, if the average waveform slope during a last fraction of each cycle (e.g., last 40%) is less than a threshold, or is less than the average slope during the first fraction of each cycle (e.g., first 60%) by a threshold amount, the processor may decide to apply quiescent period gating to the acquired imaging data. In another example, if the total fractional cycle time that the pre-max and/or post-max waveform slopes exceed the pre-determined threshold is less than a threshold value, the processor may decide to apply quiescent period gating to the acquired imaging data. In yet another example, if the ratio of low-slope to high-slope respiratory waveform data, as explained above, is below a threshold ratio, the processor may decide to apply quiescent period gating to the acquired imaging data. If none of the thresholds or set parameters are met at 712 for applying quiescent period gating, the method continues to 714 to not apply this gating to the acquired imaging data. As one example, not applying gating to the acquired imaging data may include not discarding any portion of the acquired data based on the respiratory motion waveform and/or not combining data into segmented bins and using the binned data to form an image. Instead, the method at 714 may include generating an image from all the data acquired during data acquisition and not correcting for respiratory motion effects. The method then ends. In some cases, the processor may determine to apply a different type of gating (as described above at 514) or no gating at all. If instead one or more of the set thresholds for applying quiescent period gating is met at 712, the method continues to 716 to apply quiescent period gating to the acquired image data. The method may then include generating an image from the gated image data and then displaying the resulting image via a display to a user. It should be noted that the same methods can be utilized to determine if gated processing should be applied. For instance, if the analysis determines that quiescent gating is not applicable, a secondary assessment can be performed (using some or all of the prior analysis) to determine if regular multi-bin gating should be applied, as described previously and shown in FIG. 2. This assessment can include multi-segment slope analysis between respiratory cycles to determine the similarity of bins between cycles. Further, a threshold for the similarity can be used to determine whether or not to perform gating on the acquired data. For example, the similarity of slopes within each bin for each cycle across all or multiple cycles may indicate the likelihood that applying a standard gating technique (e.g., binning) would benefit the imaging data. Said another way, the more similar the slopes in each bin across the cycles, the more consistent the data in each bin.

In this way, a type of respiratory gating (if any at all) to be applied to medical image data may be automatically determined based on a shape and slope analysis of a respiratory motion waveform obtained during acquisition of the medical imaging data. As a result, a technical effect of generating higher quality images with reduced noise and reduced image blur due to respiratory motion effects is achieved. This may also allow an accuracy of medical diagnosis based on the generated images to be increased. Additionally, determining the consistency and quiescent nature of a respiratory waveform via the slope analysis methods described herein may provide additional diagnostic tools for health providers.

In one embodiment, a method comprises acquiring imaging data with a molecular imaging apparatus; analyzing a respiratory motion waveform acquired during the acquiring imaging data; and applying gating to the acquired imaging data based on the analyzed respiratory motion waveform. In a first example of the method, the method further includes generating an image from the gated acquired imaging data and displaying the image to a user. A second example of the method optionally includes the first example and further includes wherein the respiratory motion waveform is a one-dimensional waveform acquired from the acquired imaging data. A third example of the method optionally includes one or more or both of the first and second examples, further includes wherein the respiratory motion waveform is a one-dimensional waveform acquired from a sensor coupled to a patient being scanned with the molecular imaging apparatus. A fourth example of the method optionally includes one or more or each of the first through third examples, and further includes wherein analyzing the respiratory motion waveform includes, for each cycle of the respiratory motion waveform: finding a peak amplitude of a cycle and dividing the cycle into a first segment before the peak amplitude and a second segment after the peak amplitude, where each cycle is defined between adjacent valleys of the respiratory motion waveform; determining a first slope of the first segment and a second slope of the second segment; and determining whether a difference between the first slope and the second slope is greater than a threshold. A fifth example of the method optionally includes one or more or each of the first through fourth examples, and further includes, for each cycle, marking the cycle with a first designation in response to the difference being greater than the threshold and marking the cycle with a second designation in response to the difference being less than the threshold. A sixth example of the method optionally includes one or more or each of the first through fifth examples, and further includes determining a ratio of a number of cycles with the first designation to total cycles in the respiratory motion waveform and displaying the determined ratio and the respiratory motion waveform to a user. A seventh example of the method optionally includes one or more or each of the first through sixth examples, and further includes applying gating to the acquired image data in response to the ratio being greater than a threshold. An eight example of the method optionally includes one or more or each of the first through seventh examples, and further includes not applying gating to the acquired imaging data in response to the ratio being less than a threshold and generating an image for display to a user based on the non-gated acquired image data. A ninth example of the method optionally includes one or more or each of the first through eighth examples, and further includes wherein applying gating first includes determining a type of gating to apply to the acquired image data based on the analyzed respiratory motion waveform and one or more user settings. A tenth example of the method optionally includes one or more or each of the first through ninth examples, and further includes applying a quiescent period gating to the acquired image data in response to a slope analysis of the respiratory motion waveform indicating that a quiescent-like nature of the respiratory motion waveform is greater than a threshold percentage. An eleventh example of the method optionally includes one or more or each of the first through tenth examples, and further includes applying gating to the acquired imaging data in response to a multi-segment slope analysis of the respiratory motion waveform indicating similarity in the cyclic nature of the respiratory motion waveform.

As another embodiment, a method comprises acquiring a respiratory motion waveform during imaging of a tissue; for each cycle of the acquired respiratory motion waveform, determining a first slope before a peak amplitude of a cycle and a second slope after the peak amplitude; marking each cycle of the acquired respiratory motion waveform with a first designation in response to a difference between the first slope and second slope being greater than a threshold; and displaying the marked respiratory motion waveform to a user. In a first example of the method, the method further includes determining a ratio of a number of cycles marked with the first designation to total cycles in the respiratory motion waveform and displaying the ratio to the user. A second example of the method optionally includes the first example and further includes applying gating to imaging data acquired during imaging of a tissue in response to the determined ratio being greater than a threshold. A third example of the method optionally includes one or more or both of the first and second examples, and further includes generating an image based on the gated imaging data and displaying the generated image to the user via a display. A fourth example of the method optionally includes one or more or each of the first through third examples, and further includes, in addition to displaying the marked respiratory motion waveform, displaying one or more of the determined ratio, an average of the first slope for all cycles of the respiratory motion waveform, and an average of the second slope for all cycles of the respiratory motion waveform to the user via a display. A fifth example of the method optionally includes one or more or each of the first through fourth examples, and further includes wherein the acquiring the respiratory motion waveform, determining the first slope and second slope, marking each cycle, and displaying the marked respiratory motion waveform is performed by a processor and wherein the threshold is configurable based on one or more user inputs received by the processor.

As yet another embodiment, a method comprises: acquiring imaging data with a molecular imaging apparatus; obtaining a respiratory motion waveform from the acquired imaging data; determining a quiescent-like nature of the obtained respiratory motion waveform based on a slope analysis of the waveform; and applying quiescent period gating to the acquired imaging data in response to the determined quiescent-like nature being greater than a threshold percentage. In a first example of the method, the quiescent-like nature being greater than a threshold percentage is based on one or more of an average waveform slope during a last fraction of each cycle of the obtained respiratory motion waveform being less than a first threshold, the average waveform slope during the last fraction of each cycle being less than an average waveform slope during a first remaining fraction of each cycle by a second threshold amount, a total fractional cycle time that a first slope before a peak amplitude of each cycle and/or a second slope after the peak amplitude exceeds a third threshold being less than a threshold duration, and a ratio of a low-slope to high-slope portion of data of the respiratory motion waveform being below a threshold ratio. A second example of the method optionally includes the first example and further includes generating an image based on the quiescent period gated image data and displaying the generated image to a user via a display coupled to the molecular imaging device.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring imaging data with a molecular imaging apparatus;
   analyzing a respiratory motion waveform acquired during the acquiring imaging data; and
   determining whether to apply gating to the acquired imaging data, where applying gating includes temporally dividing the acquired imaging data into groups or selecting only a portion of the acquired imaging data corresponding to a selected time period, based on the analyzed respiratory motion waveform, the determining including:
      applying gating to the acquired imaging data in response to the analyzed respiratory motion waveform meeting a pre-determined threshold or metric and generating an image from the gated acquired imaging data and displaying the generated image to a user via a display screen; and
      not applying gating to the acquired imaging data in response to the analyzed respiratory motion waveform not meeting the pre-determined threshold or metric and generating the image from the non-gated acquired imaging data and displaying the generated image to the user via the display screen;
   wherein analyzing the respiratory motion waveform includes:
   for each cycle of the respiratory motion waveform:
      finding a peak amplitude of a cycle and dividing the cycle into a first segment before the peak amplitude and a second segment after the peak amplitude, where each cycle is defined between adjacent valleys of the respiratory motion waveform;
      determining a first slope of the first segment and a second slope of the second segment; and
      determining whether a difference between the first slope and the second slope is greater than a threshold.

2. The method of claim 1, wherein the pre-determined threshold or metric includes a quiescent-like nature of the respiratory motion waveform being greater than a threshold percentage or a ratio of a number of common cycles to total cycles of the respiratory motion waveform being greater than a first threshold, the common cycles including cycles where a difference between a pre-maximum slope and a post-maximum slope is greater than a second threshold.

3. The method of claim 1, wherein the respiratory motion waveform is a one-dimensional waveform generated from the acquired imaging data and wherein the applying gating and not applying gating proceeds automatically during an imaging procedure with the molecular imaging apparatus responsive to the determining whether to apply gating.

4. The method of claim 1, wherein the respiratory motion waveform is a one-dimensional waveform acquired from a sensor coupled to a patient being scanned with the molecular imaging apparatus.

5. The method of claim 1, further comprising, for each cycle, marking the cycle with a first designation in response to the difference being greater than the threshold and marking the cycle with a second designation in response to the difference being less than the threshold.

6. The method of claim 5, further comprising determining a ratio of a number of cycles with the first designation to total cycles in the respiratory motion waveform and displaying the determined ratio and the respiratory motion waveform to the user via the display screen.

7. The method of claim 6, further comprising:
   applying gating to the acquired imaging data in response to the ratio being greater than a threshold, where applying gating includes temporally dividing the respiratory motion waveform into groups and then post-processing the imaging data acquired within a period of time corresponding to a same group together to form a composite image; and
   not applying gating to the acquired imaging data in response to the ratio being less than the threshold and generating an image for display to the user based on the non-gated acquired imaging data, where not applying gating includes not temporally dividing the respiratory motion waveform and acquired imaging data and not post-processing the acquired imaging data based on the respiratory motion waveform.

8. The method of claim 1, wherein applying gating first includes determining a type of gating to apply to the acquired imaging data based on the analyzed respiratory motion waveform and one or more user settings, the type of gating including a quiescent period gating and a standard gating.

9. The method of claim 8, further comprising applying the quiescent period gating to the acquired imaging data in response to a slope analysis of the respiratory motion waveform indicating that a quiescent-like nature of the respiratory motion waveform is greater than a threshold percentage, where applying quiescent period gating includes dividing each breath cycle of the respiratory motion waveform into a plurality of segments and only keeping the acquired imaging data taken during and corresponding to a selected segment of the plurality of segments, for each breath cycle, and discarding remaining portions of the acquired imaging data, and where the slope analysis indicates that the quiescent-like nature of the respiratory waveform is greater than the threshold percentage when a slope of the selected segment is less than a threshold.

10. The method of claim 8, further comprising applying the standard gating to the acquired imaging data in response to a multi-segment slope analysis of the respiratory motion waveform indicating similarity in a cyclic nature of the respiratory motion waveform based on a difference between a slope of a pre-maximum segment and a slope of a post-maximum segment for each breath cycle of the respiratory motion waveform, where applying the standard gating includes temporally dividing the respiratory motion waveform into bins for each breath cycle of the respiratory motion waveform and then post-processing the acquired imaging data acquired within a period of time corresponding to a same bin together to form a composite image.

11. A method, comprising:
acquiring a respiratory motion waveform and acquiring imaging data with a molecular imaging apparatus, over a same time period during imaging of a tissue;
for each cycle of the acquired respiratory motion waveform, determining a first slope before a peak amplitude of a cycle and a second slope after the peak amplitude;
marking each cycle of the acquired respiratory motion waveform with a first designation in response to a difference between the first slope and the second slope being greater than a first threshold;
displaying the marked respiratory motion waveform to a user via a display screen; and
during a first condition, in response to a determined ratio of a number of cycles marked with the first designation to total cycles in the respiratory motion waveform being greater than a second threshold, applying gating to the acquired imaging data, generating an image from the gated acquired imaging data, and displaying the generated image to the user via the display screen, where applying gating includes temporally dividing the acquired respiratory motion waveform into a plurality of bins and, for each bin of the plurality of bins, combining the imaging data acquired within a period of time corresponding to the bin into that bin, and post-processing the imaging data within a common bin together to form a composite image for displaying to the user; and
during a second condition, in response to the determined ratio being less than the second threshold, not applying gating to the acquired imaging data, generating the image from the non-gated acquired imaging data, and displaying the generated image to the user.

12. The method of claim 11, further comprising displaying the determined ratio to the user via the display screen, and wherein the total cycles includes all the marked cycles and unmarked cycles.

13. The method of claim 11, further comprising, during a third condition, in response to the determined ratio being less than the second threshold and a threshold number of cycles of the respiratory motion waveform having a quiescent period, applying quiescent period gating to the imaging data acquired during imaging of the tissue, generating the image from the quiescent period gated acquired imaging data, and displaying the generated image to the user via the display screen, where applying the quiescent period gating includes dividing each cycle of the respiratory motion waveform into a plurality of segments and only keeping the acquired imaging data taken during and corresponding to a selected segment of the plurality of segments, for each cycle, and discarding remaining portions of the acquired imaging data.

14. The method of claim 13, wherein the quiescent period of a cycle of the respiratory motion waveform is indicated by a slope of a post-maximum portion of each cycle or a slope of a portion of the post-maximum portion of each cycle.

15. The method of claim 11, further comprising, in addition to displaying the marked respiratory motion waveform, displaying one or more of the determined ratio, an average of the first slope for all cycles of the respiratory motion waveform, and an average of the second slope for all cycles of the respiratory motion waveform to the user via the display screen.

16. The method of claim 11, wherein the acquiring the respiratory motion waveform, determining the first slope and the second slope, marking each cycle, and displaying the marked respiratory motion waveform is performed by a processor, wherein the applying gating during the first condition and not applying gating during the second condition is performed automatically by the processor, and wherein the first threshold is configurable based on one or more user inputs received by the processor.

17. A method, comprising:
acquiring imaging data with a molecular imaging apparatus;
obtaining a respiratory motion waveform including a plurality of breath cycles from the acquired imaging data, wherein the imaging data and the respiratory motion waveform are acquired over a same period of time;
for each cycle of the acquired respiratory motion waveform, determining a first slope before a peak amplitude of a cycle and a second slope after the peak amplitude;
marking each cycle of the acquired respiratory motion waveform with a first designation in response to a difference between the first slope and the second slope being greater than a first threshold to obtain a slope analysis of the respiratory motion waveform;
determining a quiescent-like nature of the obtained respiratory motion waveform and whether to apply quiescent period gating to the acquired imaging data based on the slope analysis of the respiratory motion waveform, the determining the quiescent-like nature including, for each breath cycle of the respiratory motion waveform, indicating the breath cycle has a quiescent period based on a slope of one or more segments of the breath cycle;
applying quiescent period gating to the acquired imaging data in response to a threshold number of breath cycles of the respiratory motion waveform having the quiescent period, applying quiescent period gating including dividing each breath cycle of the obtained respiratory motion waveform into a plurality of segments and only keeping the acquired imaging data taken during and corresponding to a selected segment of the plurality of segments, for each breath cycle, and discarding remaining portions of the acquired imaging data; and
generating an image from the quiescent period gated imaging data, including only the non-discarded acquired imaging data, and displaying the generated image to a user via a display coupled to the molecular imaging apparatus.

18. The method of claim 17, wherein indicating the cycle has a quiescent period based on the slope of one or more segments of the breath cycle is based on one or more of an average waveform slope during a last fraction of each cycle of the obtained respiratory motion waveform being less than a first threshold, the average waveform slope during the last fraction of each cycle being less than an average waveform slope during a first remaining fraction of each cycle by a second threshold amount, a total fractional cycle time that the first slope before the peak amplitude of each cycle and/or the second slope after the peak amplitude exceeds a third threshold being less than a threshold duration, and a ratio of a low-slope to high-slope portion of data of the respiratory motion waveform being below a threshold ratio.

19. The method of claim 17, further comprising not applying quiescent period gating to the acquired imaging data in response to less than the threshold number of breath cycles of the respiratory motion waveform having the quiescent period, generating an image from the non-gated imaging data, and displaying the generated image to the user via the display coupled to the molecular imaging apparatus.

* * * * *